(12) United States Patent
Begg

(10) Patent No.: US 11,571,233 B2
(45) Date of Patent: Feb. 7, 2023

(54) TISSUE REMOVAL HANDPIECE WITH INTEGRATED SUCTION

(71) Applicant: Covidien LP, Mansfield, MA (US)

(72) Inventor: Nikolai D. Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 23 days.

(21) Appl. No.: 16/952,242

(22) Filed: Nov. 19, 2020

(65) Prior Publication Data

US 2022/0151652 A1    May 19, 2022

(51) Int. Cl.
| | |
|---|---|
| A61B 17/32 | (2006.01) |
| A61M 1/00 | (2006.01) |
| A61B 17/42 | (2006.01) |
| A61B 1/018 | (2006.01) |
| A61B 1/303 | (2006.01) |
| A61B 17/00 | (2006.01) |

(52) U.S. Cl.
CPC ........ *A61B 17/32002* (2013.01); *A61B 17/42* (2013.01); *A61M 1/80* (2021.05); *A61B 1/018* (2013.01); *A61B 1/303* (2013.01); *A61B 2017/0023* (2013.01); *A61B 2017/00199* (2013.01); *A61B 2017/00398* (2013.01); *A61B 2017/4216* (2013.01); *A61B 2217/005* (2013.01)

(58) Field of Classification Search
CPC .............. A61B 17/32002; A61B 17/42; A61B 2017/00398; A61M 1/80
See application file for complete search history.

(56) References Cited

U.S. PATENT DOCUMENTS

| | | |
|---|---|---|
| 1,585,934 A | 5/1926 | Muir |
| 1,666,332 A | 4/1928 | Hirsch |
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |

(Continued)

FOREIGN PATENT DOCUMENTS

| | | |
|---|---|---|
| CN | 102961173 A | 3/2013 |
| WO | 2010089777 A2 | 8/2010 |

OTHER PUBLICATIONS

Chinese Office Action issued in Chinese Application No. 201580072549.4 dated May 14, 2019, 10 pages.

(Continued)

*Primary Examiner* — Sarah A Simpson
(74) *Attorney, Agent, or Firm* — Carter, DeLuca & Farrell LLP

(57) ABSTRACT

A surgical handpiece for removing tissue includes a housing defining a cavity therein, the housing having a proximal hub connector disposed at a distal end thereof. An end effector assembly is operably supported by the proximal hub connector and includes an outer shaft supporting a cutting shaft configured to remove tissue upon activation thereof via translation or rotation. A fluid pump is disposed within the cavity of the housing and is configured to evacuate fluid from the cutting shaft upon activation thereof. A motor is disposed within the cavity of the housing and includes a power coupler operably coupled to both the cutting shaft and the fluid pump for suppling power thereto.

19 Claims, 3 Drawing Sheets

(56) References Cited

U.S. PATENT DOCUMENTS

| | | |
|---|---|---|
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,795 A | 7/1998 | Bays |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |

(56) References Cited

U.S. PATENT DOCUMENTS

| | | |
|---|---|---|
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,316 B1 | 1/2001 | Kovac et al. |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,663,641 B1 | 12/2003 | Kovac et al. |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,012,153 B2 | 9/2011 | Woloszko et al. |
| 8,062,214 B2 | 11/2011 | Shener et al. |
| 8,419,626 B2 | 4/2013 | Shener-Lrmakoglu et al. |
| 8,574,253 B2 | 11/2013 | Gruber et al. |
| 8,663,264 B2 | 3/2014 | Cesarini et al. |
| 8,678,999 B2 | 3/2014 | Isaacson |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 8,986,334 B2 | 3/2015 | Mark et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,107,691 B2 | 8/2015 | Fojtik |
| 9,125,550 B2 | 9/2015 | Shener-Irmakoglu et al. |
| 9,155,454 B2 | 10/2015 | Sahney et al. |
| 9,486,233 B2 | 11/2016 | Bek et al. |
| 9,913,629 B1 | 3/2018 | Sullivan et al. |
| 10,022,140 B2 | 7/2018 | Germain et al. |
| 10,631,889 B2 | 4/2020 | Brown et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2005/0085838 A1 | 4/2005 | Thompson et al. |
| 2005/0209622 A1 | 9/2005 | Carrison |
| 2005/0240206 A1 | 10/2005 | Sjostrom |
| 2006/0025793 A1* | 2/2006 | Gibson .............. A61B 17/2909 606/170 |
| 2006/0036132 A1 | 2/2006 | Renner et al. |
| 2006/0047185 A1 | 3/2006 | Shener |
| 2006/0241586 A1 | 10/2006 | Wilk |
| 2007/0213755 A1 | 9/2007 | Beckman et al. |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152611 A1 | 6/2010 | Parihar et al. |
| 2010/0152647 A1 | 6/2010 | Shener et al. |
| 2010/0312140 A1 | 12/2010 | Smith et al. |
| 2011/0166419 A1 | 7/2011 | Reif et al. |
| 2012/0078038 A1 | 3/2012 | Sahney et al. |
| 2013/0131452 A1 | 5/2013 | Kuroda et al. |
| 2013/0172870 A1 | 7/2013 | Germain et al. |
| 2013/0211321 A1 | 8/2013 | Dubois et al. |
| 2014/0031834 A1 | 1/2014 | Germain et al. |
| 2015/0305765 A1 | 10/2015 | Fojtik et al. |
| 2016/0095615 A1* | 4/2016 | Orczy-Timko .... A61B 18/1485 606/171 |
| 2017/0049441 A1 | 2/2017 | Sauer et al. |
| 2017/0105607 A1 | 4/2017 | Truckai |
| 2017/0105736 A1 | 4/2017 | Chen et al. |
| 2017/0333119 A1 | 11/2017 | Truckai |
| 2017/0360466 A1* | 12/2017 | Brown .............. A61B 17/32002 |
| 2017/0367687 A1 | 12/2017 | Hibner |
| 2020/0253628 A1 | 8/2020 | Brown et al. |
| 2021/0169512 A1* | 6/2021 | Wood ............... A61B 17/32002 |

OTHER PUBLICATIONS

International Search Report issued in corresponding International Application No. PCT/US2015/066111 dated Jun. 23, 2016, 4 pages.

Written Opinion issued in corresponding International Application No. PCT/US2015/066111 dated Jun. 23, 2016, 9 pages.

International Preliminary Report on Patentability issued in corresponding International Application No. PCT/US2015/066111 dated Jun. 20, 2017, 10 pages.

(56) References Cited

OTHER PUBLICATIONS

Australian Examination Report issue in corresponding Australian Application No. 2015364676 dated Sep. 26, 2019, 3 pages.
U.S. Appl. No. 16/593,432 to Begg et al.
Extended European Search Report issued in corresponding application EP 21207063.5 dated Mar. 29, 2022 (7 pages).

* cited by examiner

TISSUE REMOVAL HANDPIECE WITH INTEGRATED SUCTION

BACKGROUND

Technical Field

The present disclosure relates generally to surgical systems and, more particularly, outflow collection vessels, systems, and components thereof for hysteroscopic surgical procedures.

Background of Related Art

Surgical procedures, such as hysteroscopic surgical procedures, may be performed endoscopically within an organ, such as a uterus, by inserting an endoscope into the uterus and passing a tissue resection device through the endoscope and into the uterus. With respect to such hysteroscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space. The outflow fluid is collected by a collection system.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a surgical handpiece for removing tissue that includes a housing defining a cavity therein. The housing includes a proximal hub connector disposed at a distal end thereof. An end effector assembly is operably supported by the proximal hub connector and includes an outer shaft supporting a cutting shaft configured to remove tissue upon activation thereof via translation or rotation therein. A fluid pump is disposed within the cavity of the housing and is configured to evacuate fluid from the cutting shaft upon activation thereof. A motor is disposed within the cavity of the housing and includes a power coupler operably coupled to both the cutting shaft and the fluid pump for suppling power thereto.

In aspects according to the present disclosure, the fluid pump includes a passageway defined therein configured to operably connect to the end effector assembly to evacuate fluid and tissue from the cutting shaft. In other aspects according to the present disclosure, the fluid pump is a peristatic pump.

In aspects according to the present disclosure, the end effector is removably engaged to the proximal hub connector. In other aspects according to the present disclosure, the fluid pump is removably engaged to the housing. In still other aspects according to the present disclosure, the end effector and the fluid pump are removably engaged to the housing. In yet other aspects according to the present disclosure, the fluid pump is integral with the housing.

In aspects according to the present disclosure, the cutting shaft is operably coupled to an input coupler which, in turn, operably couples to an output coupler electrically coupled to the motor.

In aspects according to the present disclosure, the surgical handpiece is a tissue resection instrument.

Provided in accordance with aspects of the present disclosure is a surgical handpiece for removing tissue that includes a housing defining a cavity therein. The housing includes a proximal hub connector disposed at a distal end thereof. An end effector assembly is operably supported by the proximal hub connector and includes an outer shaft supporting a cutting shaft configured to remove tissue upon activation thereof via translation or rotation therein. A fluid pump is disposed within the cavity of the housing and is configured to evacuate fluid from the cutting shaft upon activation thereof. Aa first motor is disposed within the cavity of the housing and includes an output coupler operably coupled to the cutting shaft for suppling power thereto. A second motor is disposed within the cavity of the housing and is operably coupled to the fluid pump for suppling power thereto.

In aspects according to the present disclosure, the surgical handpiece is a tissue resection instrument.

In aspects according to the present disclosure, the first and second motors are independently activatable. In other aspects according to the present disclosure, the first and second motors are configured to cooperate with a control console for regulating power during use.

In aspects according to the present disclosure, the fluid pump is a peristaltic pump.

In aspects according to the present disclosure, the end effector is removably engaged to the proximal hub connector. In other aspects according to the present disclosure, the fluid pump is removably engaged to the housing. In still other aspects according to the present disclosure, the end effector and the fluid pump are removably engaged to the housing. In yet other aspects according to the present disclosure, the fluid pump is integral with the housing.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
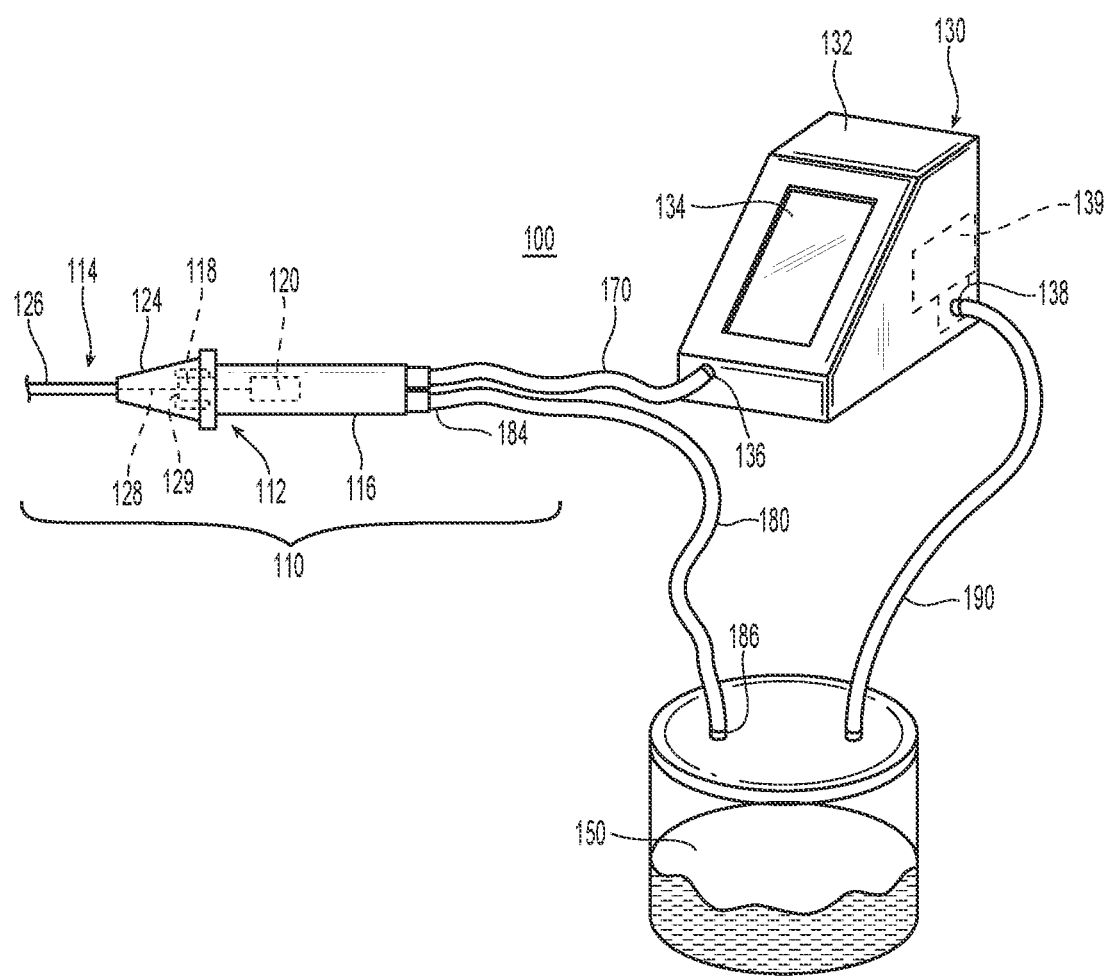
FIG. 1 is a perspective view of a surgical system configured for use in a hysteroscopic surgical procedure.

Referring to FIG. 1, a surgical system provided in accordance with aspects of the present disclosure is shown generally identified by reference numeral 100. Surgical system 100 includes a surgical instrument 110, a control console 130, and a collection vessel 150. Surgical system 100 further includes a cable 170, outflow tubing 180, and vacuum tubing 190. Surgical system 100 may further include an endoscope (not shown), e.g., a hysteroscope, defining a working channel for inserting of surgical instrument 110 therethrough, and adapted to connect to inflow tubing (not shown) to supply fluid to an internal surgical site and/or additional outflow tubing (not shown) to return fluid to collection vessel 150.

Surgical instrument 110 includes a handpiece 112 that may be configured as a reusable component and an end effector assembly 114 that may be configured as a single-use, disposable component. Handpiece 112 includes a housing 116 to facilitate grasping and manipulation of surgical instrument 110 by a user. Handpiece 112 further includes an output coupler 118 configured to operably engage end effector assembly 114, a motor 120 disposed within housing 116 and operably coupled to output coupler 118 to drive output coupler 118 and, thus, drive end effector assembly 114. Cable 170 electrically couples handpiece 112 and control console 130 with one another and, more specifically, electrically couples control console 130 with motor 120 to power and control operation of motor 120 and electrically couples control console 130 with a storage device(s), e.g., a microchip(s) (not explicitly shown), associated with handpiece 112 and/or end effector assembly 114 to enable communication of, for example, identification, setting, and control information therebetween. In embodiments, cable 170 is fixedly attached to handpiece 112 and releasably couplable with control console 130, although other configurations are also contemplated.

Continuing with reference to FIG. 1, end effector assembly 114 includes a proximal hub 124 configured to releasably engage housing 116 of handpiece 112 to releasably mechanically engage end effector assembly 114 with handpiece 112. End effector assembly 114 further includes an outer shaft 126 extending distally from proximal hub 124 and a cutting shaft 128 extending through outer shaft 126. A proximal end of cutting shaft 128 extends into proximal hub 124 wherein an input coupler 129 is engaged with cutting shaft 128. Input coupler 129 is configured to operably couple to output coupler 118 of handpiece 112 when proximal hub 124 is engaged with housing 116 such that, when motor 120 is activated to drive output coupler 118, input coupler 129 is driven in a corresponding manner to thereby move cutting shaft 128 within and relative to outer shaft 126.

Outer shaft 126, as noted above, extends distally from proximal hub 124 and, in embodiments, is stationary relative to proximal hub 124, although other configurations are also contemplated. Outer shaft 126 may define a window (not shown) through a side wall thereof towards a distal end thereof to provide access to cutting shaft 128 which is rotatably and/or translatably disposed within outer shaft 126. Cutting shaft 128 may define an opening (not shown) towards the distal end thereof providing access to the interior thereof and may include a serrated cutting edge (not shown) surrounding the opening, although other suitable cutting edge configurations are also contemplated. Alternatively, or additionally, outer shaft 126 may include a cutting edge defined about the window thereof.

Motor 120, as noted above, is activated to move cutting shaft 128 and, more specifically, to drive rotation and/or translation of cutting shaft 128 relative to outer shaft 126. Control console 130, coupled to motor 120 via cable 170, enables selective powering and controlling of motor 120 and, thus, selective rotation and/or translation of cutting shaft 128 relative to outer shaft 126 to resect tissue adjacent the distal end of end effector assembly 114. Control console 130 is detailed below.

Outflow tubing 180 includes a distal end 184 configured to releasably couple to handpiece 112 and a proximal end 186 configured to couple to collection vessel 150. More specifically, handpiece 112 defines an internal passage (not shown) that couples distal end 184 of outflow tubing 180 with the interior of cutting shaft 128 in fluid communication with the interior of cutting shaft 128 such that fluid, tissue, and debris drawn into cutting shaft 128 and/or outer shaft 126 may be suctioned, under vacuum, e.g., from vacuum pump 139 of control console 130, through end effector assembly 114, handpiece 112, and outflow tubing 180 to collection vessel 150.

Referring still to FIG. 1, collection vessel 150, as noted above, is coupled to proximal end 186 of outflow tubing 180 to receive the fluid, tissue, and debris suctioned through end effector assembly 114 and outflow tubing 180. Vacuum tubing 190 is coupled between collection vessel 150 and a vacuum source, e.g., vacuum pump 139 of control console 130, such that, upon activation of vacuum pump 139, negative pressure is established through collection vessel 150, outflow tubing 180, and the interior of cutting shaft 128 of end effector assembly 114 to draw the fluids, tissue, and debris into and through cutting shaft 128, handpiece 112, outflow tubing 180, and into collection vessel 150.

Control console 130 generally includes an outer housing 132, a touch-screen display 134 accessible from the exterior of outer housing 132, a cable port 136 configured to receive cable 170, a vacuum tubing port 138 configured to receive vacuum tubing 190, and a vacuum pump 139 disposed within outer housing 132 and operably coupled with vacuum port 138. Outer housing 132 further houses internal electronics (not shown) of control console 130. Control console 130 may be configured to connect to a mains power supply (not shown) for powering control console 130. Further, control console 130 may be configured to receive user input, e.g., use information, setting selections, etc., via touch-screen display 134 or a peripheral input device (not shown) coupled to control console 130. Operational input, e.g., ON/OFF signals, power level settings (HI power vs. LO power), etc., may likewise be input via touch-screen display 134 or a peripheral input device (not shown) such as, for example, a footswitch (not shown), a hand switch (not shown) disposed on handpiece 112, etc.

In use, upon an activation input provided to control console 130, control console 130 powers and controls motor 120 of handpiece 112 to, in turn, drive cutting shaft 128 of end effector assembly 114 to resect tissue adjacent the distal end of end effector assembly 114, while vacuum pump 139 of control console 130 suctions fluid, the resected tissue, and debris through cutting shaft 128, handpiece 112, outflow tubing 180, and into collection vessel 150.

Collection vessel 150 may define various different configurations and/or may be utilized with various different components to define a collection system. Such collection vessels and systems are provided in accordance with the present disclosure and detailed below with reference to commonly-owned U.S. patent application Ser. No. 16/593, 432 the entire contents of which being incorporated by reference herein. As an alternative to use with surgical system 100, the collection vessels and systems of the present disclosure may be utilized within any other suitable surgical system.

Figure 2:
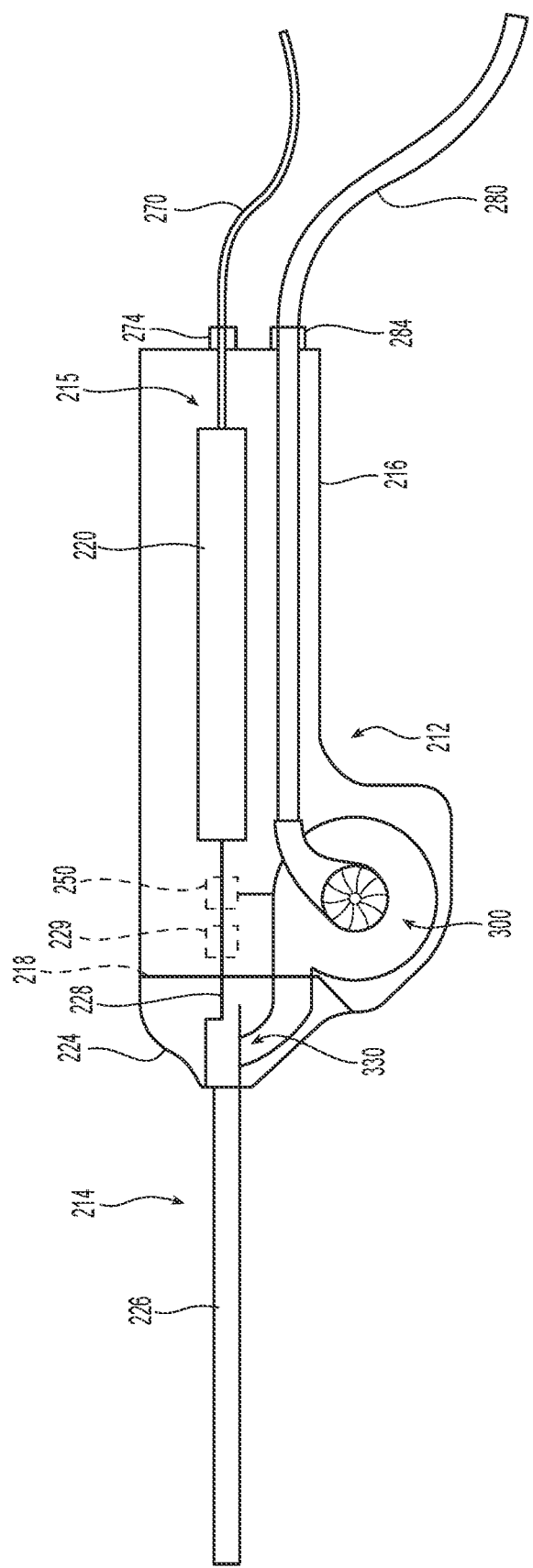
FIG. 2 is side schematic view of a surgical handpiece for use with the system shown in FIG. 1.

With reference to FIG. 2, another embodiment of a surgical handpiece 212 is shown and includes similar elements as described above and, as such, only those necessary to describe the differences between handpiece 112 and handpiece 212 will be described in detail. Surgical handpiece 212 may be configured as a reusable component along with end effector assembly 214 that may be configured as a single-use or disposable component. Handpiece 212 includes a housing 216 to facilitate grasping and manipulation thereof by a user. Handpiece 212 further includes an output coupler 218 configured to operably engage end effector assembly 214, a motor 220 disposed within housing 216 and operably coupled to output coupler 218 to drive output coupler 218 and, thus, drive end effector assembly 214.

Cable 270 electrically couples handpiece 212 at coupling 274 and control console, e.g., control console 130, with one another and, more specifically, electrically couples control console 130 with motor 220 to power and control operation of motor 220 and electrically couples control console 130 with one or more storage devices as explained above with respect t to FIG. 1. This enables communication between handpiece 212 and/or end effector assembly 214, e.g., identification, setting, and control information.

Continuing with reference to FIG. 2, end effector assembly 214 includes a proximal hub 224 configured to releasably engage housing 216 of handpiece 212 to releasably mechanically engage end effector assembly 214 with handpiece 212. End effector assembly 214 further includes an outer shaft 226 extending distally from proximal hub 224 and a cutting shaft 228 extending through outer shaft 226. A proximal end of cutting shaft 228 extends into proximal hub 224 wherein an input coupler 229 is engaged with cutting shaft 228. Input coupler 229 is configured to operably couple to output coupler 218 of handpiece 212 when proximal hub 224 is engaged with housing 216 such that, when motor 220 is activated to drive output coupler 218, input coupler 229 is driven in a corresponding manner to thereby move cutting shaft 228 within and relative to outer shaft 226.

Motor 220, as noted above, is activated to move cutting shaft 228 and, more specifically, to drive rotation and/or translation of cutting shaft 228 relative to outer shaft 226. Control console 130 (FIG. 1), coupled to motor 220 via cable 270, enables selective powering and controlling of motor 220 and, thus, selective rotation and/or translation of cutting shaft 228 relative to outer shaft 226 to resect tissue adjacent the distal end of end effector assembly 214. In this embodiment, the motor 220 is also configured to power a fluid pump 300 disposed within the housing 216.

More particularly, outflow tubing 280 includes a distal end 284 configured to releasably couple to handpiece 212 and a proximal end (not shown but similar to proximal end 186) configured to couple to collection vessel 150 (FIG. 1). Handpiece 212 may define an internal passage (not shown) that couples distal end 284 of outflow tubing 280 with the interior of cutting shaft 228 in fluid communication with the interior of cutting shaft 228 such that fluid, tissue, and debris drawn into cutting shaft 228 and/or outer shaft 226 may be suctioned, under vacuum, e.g., from fluid pump 300 through end effector assembly 214, handpiece 212, and outflow tubing 280 to collection vessel 150. Outflow tube 280 may include multiple tubes (not shown) disposed therein to provide both fluid to cutting shaft 228 and suction from cutting shaft 228 depending upon particular purpose. On the other hand, the fluid may be supplied through the interior cavity 215 defined within housing 216 and suctioned out through passageway 330 defined at a proximal end of outer shaft 226 or cutting shaft 228.

A power coupler 250 is electrically coupled the input coupler 229 and the motor 220 and supplies power to both the input coupler 229 and the fluid pump 300. In this fashion, a single motor 220 may be utilized to power both the input coupler 229 (cutting shaft 228) and the fluid pump 300.

Fluid pump 300 may be integrally associated with housing 216 or may be removably coupled thereto in the form of a cartridge or the like. In embodiments, both the cutting assembly, e.g., cutting shaft 228 and outer shaft 226, may be removably engaged to the proximal hub 224 along with the fluid pump 300 enabling the entire unit to be disposable relative to the remainder of the handpiece 212. In other embodiment, the fluid pump 300, the cutting shaft 228 and the outer shaft may be individually separable from the handpiece 212 or one another depending upon a particular purpose.

Outer shaft 226 is similar to outer shaft 126 noted above and extends distally from proximal hub 224 and, in embodiments, is stationary relative to proximal hub 224, although other configurations are also contemplated. Outer shaft 226 may define a window (not shown) through a side wall thereof towards a distal end thereof to provide access to cutting shaft 228 which is rotatably and/or translatably disposed within outer shaft 226. Cutting shaft 228 may define an opening (not shown) towards the distal end thereof providing access to the interior thereof and may include a serrated cutting edge (not shown) surrounding the opening, although other suitable cutting edge configurations are also contemplated. Alternatively, or additionally, outer shaft 226 may include a cutting edge defined about the window thereof.

Motor 220, as noted above, is activated to move cutting shaft 228 and, more specifically, to drive rotation and/or translation of cutting shaft 228 relative to outer shaft 226. A control console, e.g., control console 130, coupled to motor 220 enables selective powering and controlling of motor 220 and, thus, selective rotation and/or translation of cutting shaft 228 relative to outer shaft 226 to resect tissue adjacent the distal end of end effector assembly 214. Control console 130 is detailed above.

As the pump 300 and cutting shaft 228 are driven by activation of motor 220, suction is applied to the cutting shaft 228 to aid in the resection and tissue evacuation and fluid and tissue are driven into the passageway 330 and outflow tubing 280 to be collected by the specimen container 150.

Figure 3:
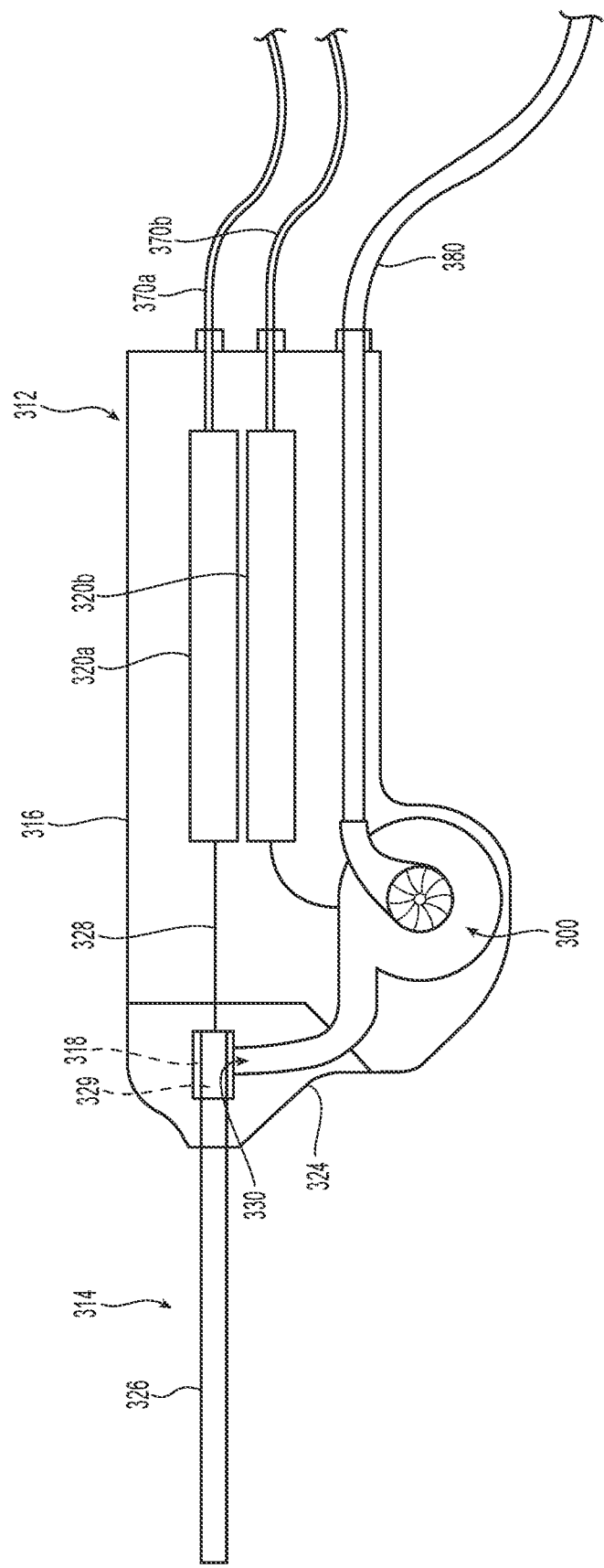
FIG. 3 is side schematic view of another embodiment of a surgical handpiece for use with the system shown in FIG. 1.

With reference to FIG. 3, another embodiment of a surgical handpiece 312 is shown and includes similar elements as described above and, as such, only those necessary to describe the differences between handpiece 112, 212 and handpiece 312 will be described in detail. Similar to the handpieces described above, surgical handpiece 312 may be configured as a reusable component along with end effector assembly 314 that may be configured as a single-use or disposable component. Handpiece 312 includes a housing 316 to facilitate grasping and manipulation thereof by a user. Handpiece 312 further includes an output coupler 318 configured to operably engage end effector assembly 314, a motor 320a disposed within housing 316 and operably coupled to output coupler 318 to drive output coupler 318 and, thus, drive end effector assembly 314 and a motor 320b operably coupled to the fluid pump 300.

Cable 370a electrically couples handpiece 312 and control console, e.g., control console 130, with one another and, more specifically, electrically couples control console 130 with motor 320a to power and control operation of motor 320a and electrically couples control console 130 with one or more storage devices as explained above with respect t to FIG. 1. This enables communication between handpiece 312 and/or end effector assembly 314, e.g., identification, setting, and control information.

Continuing with reference to FIG. 3, end effector assembly 314 includes a proximal hub 324 configured to releasably engage housing 316 of handpiece 312 to releasably mechanically engage end effector assembly 314 with handpiece 312. End effector assembly 314 further includes an outer shaft 326 extending distally from proximal hub 324 and a cutting shaft 328 extending through outer shaft 326. A proximal end of cutting shaft 328 extends into proximal hub 324 wherein an input coupler 329 is engaged with cutting shaft 328. Input coupler 329 is configured to operably couple to output coupler 318 of handpiece 312 when proximal hub 324 is engaged with housing 316 such that, when motor 320a is activated to drive output coupler 318, input coupler 329 is driven in a corresponding manner to thereby move cutting shaft 328 within and relative to outer shaft 326.

Motor 320a, as noted above, is activated to move cutting shaft 328 and, more specifically, to drive rotation and/or translation of cutting shaft 328 relative to outer shaft 326. Control console 130 (FIG. 1), coupled to motor 320a via cable 370a, enables selective powering and controlling of motor 320a and, thus, selective rotation and/or translation of cutting shaft 328 relative to outer shaft 326 to resect tissue adjacent the distal end of end effector assembly 314. Outer shaft 326 is similar to outer shaft 126, 226 noted above with respect to FIGS. 1 and 2.

Outflow tubing 380 includes a distal end 384 configured to releasably couple to handpiece 212 and a proximal end (not shown but similar to proximal end 186) configured to couple to collection vessel 150 (FIG. 1). Handpiece 312 may define an internal passage (not shown) that couples distal end 384 of outflow tubing 380 with the interior of cutting shaft 328 in fluid communication with the interior of cutting shaft 328 such that fluid, tissue, and debris drawn into cutting shaft 328 and/or outer shaft 326 may be suctioned, under vacuum, e.g., from fluid pump 300 through end effector assembly 314, handpiece 312, and outflow tubing 380 to collection vessel 150. Outflow tube 380 may include multiple tubes (not shown) disposed therein the provide both fluid to cutting shaft 328 and suction from cutting shaft 328 depending upon particular purpose. On the other hand, the fluid may be supplied through the interior of housing 316 and suctioned out through passageway 330 defined at a proximal end of outer shaft 326 or cutting shaft 328.

Fluid pump 300 may be integrally associated with housing 316 or may be removably coupled thereto in the form of a cartridge or the like. In embodiments, both the cutting assembly, e.g., cutting shaft 328 and outer shaft 326, may be removably engaged to the proximal hub 324 along with the fluid pump 300 enabling the entire unit to be disposable relative to the remainder of the handpiece 312. In other embodiment, the fluid pump 300, the cutting shaft 328 and the outer shaft 326 may be individually separable from the handpiece 312 or one another depending upon a particular purpose. The output tubing 380 may be removably engageable with the fluid pump 300.

Motor 320b is included and is configured to supply power to fluid pump 300. Motor 320b may be connected via cable 370b to the same control console, e.g., control console 130 as noted above, or may be connected to a separate control console (not shown). Motor 320b is activatable to control the fluid pump 300 and may be electrically coupled to motor 320a for simultaneous or sequential activation or may be stand alone and independently activated.

As the pump 300 is driven by activation of motor 320b and the cutting shaft 228 is driven by activation of motor 320a, suction is applied to the cutting shaft 328 to aid in the resection and tissue evacuation and fluid and tissue are driven into the passageway 330 and outflow tubing 380 to be collected by the specimen container 150. In aspects according to the present disclosure, the fluid pump 300 is a peristaltic pump While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical handpiece for removing tissue, comprising:
a housing defining a cavity therein;
a proximal hub connector removably coupled to a distal end of the housing;
an end effector assembly removably coupled to the proximal hub connector, the end effector assembly including an outer shaft supporting a cutting shaft configured to remove tissue upon activation thereof via at least one of translation or rotation therein;
a fluid pump disposed within the cavity of the housing, the fluid pump configured to evacuate fluid from the cutting shaft upon activation thereof; and
a motor disposed within the cavity of the housing, the motor including a power coupler operably coupled to both the cutting shaft and the fluid pump for suppling power thereto.

2. The surgical handpiece for removing tissue according to claim 1, wherein the fluid pump includes a passageway defined therein configured to operably connect to the end effector assembly to evacuate fluid and tissue from the cutting shaft.

3. The surgical handpiece for removing tissue according to claim 1, wherein the fluid pump is a peristaltic pump.

4. The surgical handpiece for removing tissue according to claim 1, wherein the fluid pump is configured to be removed from within the cavity of the housing.

5. The surgical handpiece for removing tissue according to claim 1, wherein the end effector assembly and the fluid pump are removably engaged to the housing.

6. The surgical handpiece for removing tissue according to claim 1, wherein the fluid pump is integral with the housing.

7. The surgical handpiece for removing tissue according to claim 1, wherein the surgical handpiece is a tissue resection instrument.

8. A surgical handpiece for removing tissue, comprising:
a housing defining a cavity therein;
a proximal hub connector removably coupled to a distal end of the housing;
an end effector assembly removably coupled to the proximal hub connector, the end effector assembly including an outer shaft supporting a cutting shaft configured to remove tissue upon activation thereof via at least one of translation or rotation therein;
a fluid pump disposed within the cavity of the housing, the fluid pump configured to evacuate fluid from the cutting shaft upon activation thereof;
a first motor disposed within the cavity of the housing, the first motor including an output coupler operably coupled to the cutting shaft for suppling power thereto; and
a second motor disposed within the cavity of the housing, the second motor operably coupled to the fluid pump for suppling power thereto.

9. The surgical handpiece for removing tissue according to claim 8, wherein the surgical handpiece is a tissue resection instrument.

10. The surgical handpiece for removing tissue according to claim 9, wherein the first and second motors are independently activatable.

11. The surgical handpiece for removing tissue according to claim 8, wherein the first and second motors are configured to cooperate with a control console for regulating power during use.

12. The surgical handpiece for removing tissue according to claim 8, wherein the fluid pump is a peristaltic pump.

13. The surgical handpiece for removing tissue according to claim 8, wherein the fluid pump is configured to be removed from within the cavity of the housing.

14. The surgical handpiece for removing tissue according to claim 8, wherein the end effector assembly and the fluid pump are removably engaged to the housing.

15. The surgical handpiece for removing tissue according to claim 8, wherein the fluid pump is integral with the housing.

16. The surgical handpiece for removing tissue according to claim 1, further comprising an input coupler disposed within the proximal hub connector and removably coupled to a proximal end portion of the cutting shaft.

17. The surgical handpiece for removing tissue according to claim 16, further comprising an output coupler disposed within the cavity of the housing and electrically coupled to the motor, the output coupler configured to couple to the input coupler when the proximal hub connecter is coupled to the distal end of the housing such that activation of the motor drives the output coupler to cause the input coupler to move the cutting shaft relative to the outer shaft for resecting tissue.

18. The surgical handpiece for removing tissue according to claim 8, further comprising an input coupler disposed within the proximal hub connector and removably coupled to a proximal end portion of the cutting shaft.

19. The surgical handpiece for removing tissue according to claim 18, further comprising an output coupler disposed within the cavity of the housing and electrically coupled to the first motor, the output coupler configured to couple to the input coupler when the proximal hub connecter is coupled to the distal end of the housing such that activation of the first motor drives the output coupler to cause the input coupler to move the cutting shaft relative to the outer shaft for resecting tissue.

* * * * *